United States Patent
Hong

(10) Patent No.: US 12,117,403 B2
(45) Date of Patent: Oct. 15, 2024

(54) GEMSTONE PLANNING

(71) Applicant: De Beers UK Ltd, London (GB)

(72) Inventor: Qi He Hong, Surrey (GB)

(73) Assignee: De Beers UK Ltd, London (GB)

( * ) Notice: Subject to any disclaimer, the term of this patent is extended or adjusted under 35 U.S.C. 154(b) by 496 days.

(21) Appl. No.: 17/620,434

(22) PCT Filed: May 21, 2020

(86) PCT No.: PCT/EP2020/064217
§ 371 (c)(1),
(2) Date: Dec. 17, 2021

(87) PCT Pub. No.: WO2020/254056
PCT Pub. Date: Dec. 24, 2020

(65) Prior Publication Data
US 2022/0349830 A1 Nov. 3, 2022

(30) Foreign Application Priority Data
Jun. 20, 2019 (GB) ...................................... 1908866

(51) Int. Cl.
*G06V 20/64* (2022.01)
*A44C 17/00* (2006.01)
(Continued)

(52) U.S. Cl.
CPC ............ *G01N 21/87* (2013.01); *A44C 17/00* (2013.01); *A44C 17/001* (2013.01); *G06T 17/00* (2013.01);
(Continued)

(58) Field of Classification Search
CPC ....... G06T 17/00; G06T 17/20; G06T 17/205; G06T 17/30; G06T 17/10; G06T 19/00;
(Continued)

(56) References Cited

U.S. PATENT DOCUMENTS 4,783,829 A * 11/1988 Miyakawa ............. G06V 20/66
382/209
6,048,813 A * 4/2000 Hunter .................... C30B 29/36
501/86
(Continued)

FOREIGN PATENT DOCUMENTS

CN 1404016 A * 3/2003
JP 2016193196 A * 11/2016 ............. A61B 6/466
(Continued)

OTHER PUBLICATIONS

Search machine translation: Human Face Fusion Multi-view And Multi-thread Two-dimensional Information Of Establishing Method Of Three-dimensional Model of CN 1404016 to Xu et al., translated Jun. 11, 2024, 41 pages. (Year: 2024).*
(Continued)

*Primary Examiner* — Matthew C Bella
*Assistant Examiner* — Dennis Rosario

(57) ABSTRACT

A method of determining an optimal target gemstone to be obtained from a rough gemstone comprises obtaining a first series of 2D images of the rough gemstone; providing a 3D model of a target gemstone to be obtained from the rough gemstone; and generating a second series of 2D images of the target gemstone from the 3D model thereof. The method then comprises comparing the first and second series of 2D images to determine an optimal transformation to be applied to the 3D model of the target gemstone.

21 Claims, 5 Drawing Sheets

(51) Int. Cl.
| | | |
|---|---|---|
| *G01N 21/87* | (2006.01) | |
| *G06T 17/00* | (2006.01) | |
| *G06T 19/00* | (2011.01) | |
| *G06T 19/20* | (2011.01) | |
| *G06V 10/75* | (2022.01) | |
| *H04N 13/275* | (2018.01) | |
| *H04N 13/395* | (2018.01) | |

(52) U.S. Cl.
CPC .............. *G06T 19/00* (2013.01); *G06T 19/003* (2013.01); *G06T 19/006* (2013.01); *G06T 19/20* (2013.01); *G06V 10/75* (2022.01); *G06V 20/647* (2022.01); *H04N 13/275* (2018.05); *H04N 13/395* (2018.05); *G06T 2219/00* (2013.01); *G06T 2219/008* (2013.01); *G06T 2219/2004* (2013.01); *G06T 2219/2021* (2013.01)

(58) Field of Classification Search
CPC .......... G06T 19/20; G06T 2207/10028; G06T 19/003; G06T 2200/08; G06T 2219/2016; G06T 7/30; G06T 7/32; G06T 7/344; G06T 7/37; G06T 7/38; G06T 2207/30168; G06T 2207/30108; G06T 2207/30132; G06T 2207/30164; G06T 3/00; G06T 3/14; G06T 3/40; G06T 3/06; G06T 3/067; G06T 7/0002; G06T 7/0004; G06T 7/0006; G06T 7/0008; G06T 7/001; G06T 3/073; G06T 3/16; G06T 7/168; G06T 3/60; G06T 7/251; G06T 19/006; G06T 2219/2021; G06T 2219/20; G06T 2219/00; G06T 2219/008; G06T 2219/2004; G06T 7/75; G06T 7/50; G06T 7/564; G06T 7/64; G06T 7/13; G06T 9/20; G06T 7/254; G06F 18/22; G06F 30/20; G06F 2119/18; G06F 2119/00; G06F 2119/22; G06V 20/647; G06V 20/653; G06V 20/66; G06V 10/248; G06V 10/24; G06V 10/74; G06V 10/75; G06V 10/753; G06V 10/755; G06V 10/7553; G06V 10/7557; G06V 10/759; G06V 10/758; G06V 10/757; G06V 10/754; G06V 10/752; G06V 10/751; G06V 10/7515; G06V 20/698; G06V 10/761; G06V 40/162; G06V 40/197; G06V 2201/07; G06V 20/64; H04N 13/282; H04N 13/204; H04N 13/117; H04N 13/111; H04N 13/139; H04N 13/207; H04N 23/45; H04N 13/239; H04N 21/8146; H04N 2213/003; H04N 5/2628; H04N 13/275; H04N 13/279; H04N 13/395; H04N 13/393; G06Q 30/0631; G06Q 30/0643; A44C 17/00; A44C 17/001; A44C 17/04

See application file for complete search history.

(56) References Cited

U.S. PATENT DOCUMENTS

| | | | |
|---|---|---|---|
| 6,333,749 | B1 * | 12/2001 | Reinhardt ................. G06T 7/75 345/619 |
| 2006/0062446 | A1 | 3/2006 | Porat |
| 2006/0066877 | A1 | 3/2006 | Benzano |
| 2012/0274751 | A1 * | 11/2012 | Smith ..................... G01N 21/87 348/E5.029 |
| 2014/0107986 | A1 | 4/2014 | Sivovolenko et al. |
| 2015/0294492 | A1 * | 10/2015 | Koch ................... H04N 13/111 345/426 |
| 2018/0253877 | A1 * | 9/2018 | Kozub ....................... G06T 5/50 |
| 2021/0129286 | A1 * | 5/2021 | Sivovolenko ......... G06T 1/0014 |

FOREIGN PATENT DOCUMENTS

| | | |
|---|---|---|
| WO | 2006/087702 A1 | 8/2006 |
| WO | 2009/068354 A1 | 6/2009 |

OTHER PUBLICATIONS

Search machine translation: Medical Image Processor of JP 2016-193196 A to Wahrenberg, translated Jun. 11, 2024, 42 pages. (Year: 2024).*

International Preliminary Report on Patentability for Application No. PCT/EP2020/064217, mailed on Dec. 30, 2021, 8 pages.

International Search Report and Written Opinion for PCT Application No. PCT/EP2020/064217, mailed on Aug. 14, 2020, 11 pages.

Search Report for Application No. GB1908866.5 mailed on Nov. 15, 2019, 3 pages.

* cited by examiner

S1

S2

GEMSTONE PLANNING

This application is a National Phase Application of International Patent Application No. PCT/EP2020/064217, filed on May 21, 2020, which is based on and claims priority to and benefits of British Patent Application GB 1908866.5, entitled "GEMSTONE PLANNING" and filed on Jun. 20, 2019. The entire content of all of the above identified applications is incorporated herein by reference.

TECHNICAL FIELD

The present invention relates to a method of determining an optimal target gemstone to be obtained from a rough gemstone, such as a diamond.

BACKGROUND

It is often desirable to cut and polish a rough gemstone, such as a diamond, to form facets which reveal the natural beauty of the stone. In order to produce the best possible cut and faceted stone from a rough stone, the cutting process needs to be carefully planned to ensure maximum yield and minimum wastage.

For this reason, it is known to produce an initial three-dimensional (3D) virtual model of the rough stone which can then be imported into industry-standard planning software (e.g. Sarine DiaExpert®). This software can calculate the optimal position of the "target" gemstone i.e. the faceted cut stone that will be produced from the rough stone. Methods of producing an initial 3D model of a rough gemstone may include imaging the stone while it is rotated under collimated lighting conditions.

The planning software typically calculates the optimal target gemstone based on various parameters, such as required yield, and outputs a second 3D model which comprises a representation of the rough stone in addition to the target gemstone that is planned to be cut from it. Further bruiting and polishing is usually required after the cutting process is complete, in order to produce the final number of planned facets on the target gemstone.

FIG. 1 illustrates an exemplary 3D model 10 which may be output by the planning software. The 3D model 10 includes an original, uncut rough stone 20 and a target, brilliant-cut gemstone 30 to be produced from the rough stone.

One problem with the planning process described above is that the computational manipulation of a highly-detailed, virtual 3D model of a rough gemstone, and the calculation required to determine an optimal target gemstone to be cut from it, may be highly resource-intensive in terms of CPU processing time and bandwidth.

SUMMARY

In one aspect of the present invention there is provided a method of determining an optimal target gemstone to be obtained from a rough gemstone, the method comprising: obtaining a first series of two-dimensional (2D) images of the rough gemstone; providing a 3D model of a target gemstone to be obtained from the rough gemstone; generating a second series of 2D images of the target gemstone from the 3D model thereof; and comparing the first and second series of 2D images to determine an optimal transformation to be applied to the 3D model of the target gemstone.

The first and second series of 2D images are preferably obtained from the same positions.

Optionally, the 2D images are silhouette images.

The method may further comprise correlating the first and second series of 2D images before carrying out the comparing step. Correlating the first and second series of 2D images may comprise setting a geometric centre of the 3D model of the target gemstone to be coincident with an image centre of each of the first series of 2D images.

Obtaining the first series of 2D images of the rough gemstone may comprise illuminating the rough gemstone with collimated light and capturing a 2D image of the rough gemstone at each of a plurality of discrete rotational increments. The method may comprise rotating the gemstone as the first series of 2D images is obtained. A further series of 2D images of the rough gemstone may be obtained under diffuse lighting, each further 2D image captured at each of the plurality of discrete rotational increments.

Obtaining the first series of 2D images of the rough gemstone may comprise generating 2D images from a 3D model of the rough gemstone.

Providing the 3D model of the target gemstone may comprise selecting a 3D model from a plurality of existing 3D models of cut and faceted gemstones.

Generating a second series of 2D images of the target gemstone from the 3D model thereof may comprise virtually positioning a plurality of virtual cameras around the 3D model of the target gemstone, each virtual camera configured to capture one or more 2D images of the target gemstone from its respective position.

The plurality of virtual cameras may be positioned in in a geodesic arrangement around the 3D model of the target gemstone.

The method may comprise virtually illuminating the 3D model of the target gemstone with collimated light.

Comparing the first and second series of 2D images to determine an optimal transformation to be applied to the 3D model of the target gemstone may comprise projecting each 2D image of the second series of 2D images into the corresponding 2D image of the first series of 2D images, wherein the corresponding 2D images of the first and second series of 2D images are captured from the same position; determining a first scaling factor, which when applied to each of the second series of 2D images produces a scaled second series of 2D images, each of which is too large to fit inside the corresponding 2D image of the first series; determining a second scaling factor, which when applied to the each of the second series of 2D images produces a scaled series of 2D images, each of which fits inside the corresponding 2D image of the first series.

Comparing the first and second series of 2D images to determine an optimal transformation to be applied to the 3D model of the target gemstone may further comprise determining the average of the first and second scaling factors to produce a third scaling factor; applying the third scaling factor to the 3D model of the target gemstone to generate a scaled 3D model; determining all possible combinations of translational and rotational transformations of the 3D model of the target gemstone; for each combination, generating a series of transformed and scaled 2D images of the target gemstone from the scaled 3D model; for each combination, projecting each 2D image of the series of transformed and scaled 2D images into the corresponding 2D image of the first series of 2D images; and iteratively increasing or decreasing the third scaling factor until a combination is identified wherein each of the 2D images of the series of transformed and scaled 2D images fits within the corresponding 2D image of the first series, and wherein the difference between the first and the second scaling factors is smaller than a predetermined threshold.

The method may comprise applying the identified combination of translational, rotational and scaling transformations to the 3D model of the target gemstone.

The optimal target gemstone may correspond to the largest target gemstone that is obtainable from the rough gemstone.

Optionally, the rough gemstone is a diamond.

The method may comprise generating a 3D model of the rough gemstone that comprises the optimal target gemstone to be obtained from the rough gemstone.

In another aspect of the present invention there is provided a method of determining an optimal target gemstone to be obtained from a rough gemstone, the method comprising: obtaining a first series of 2D images of the rough gemstone; providing a 3D model of a target gemstone to be obtained from the rough gemstone; generating a second series of 2D images of the target gemstone from the 3D model thereof; and fitting each image of the second series of 2D images into a corresponding image of the first series of 2D images to determine if the target gemstone will fit into the rough gemstone.

Corresponding images of the first and second series of 2D images preferably comprise images captured from the same position.

In a still further aspect of the present invention there is provided an apparatus for determining an optimal target gemstone to be obtained from a rough gemstone, the apparatus comprising: one or more image capture devices configured to obtain a first series of 2D silhouette images of the rough stone; and a processor configured to: generate a second series of virtual 2D silhouette images from a 3D model of a target gemstone to be obtained from the rough gemstone; and compare the first and second series of 2D images to determine an optimal transformation to be applied to the 3D model of the target gemstone.

DETAILED DESCRIPTION

Figure 1:
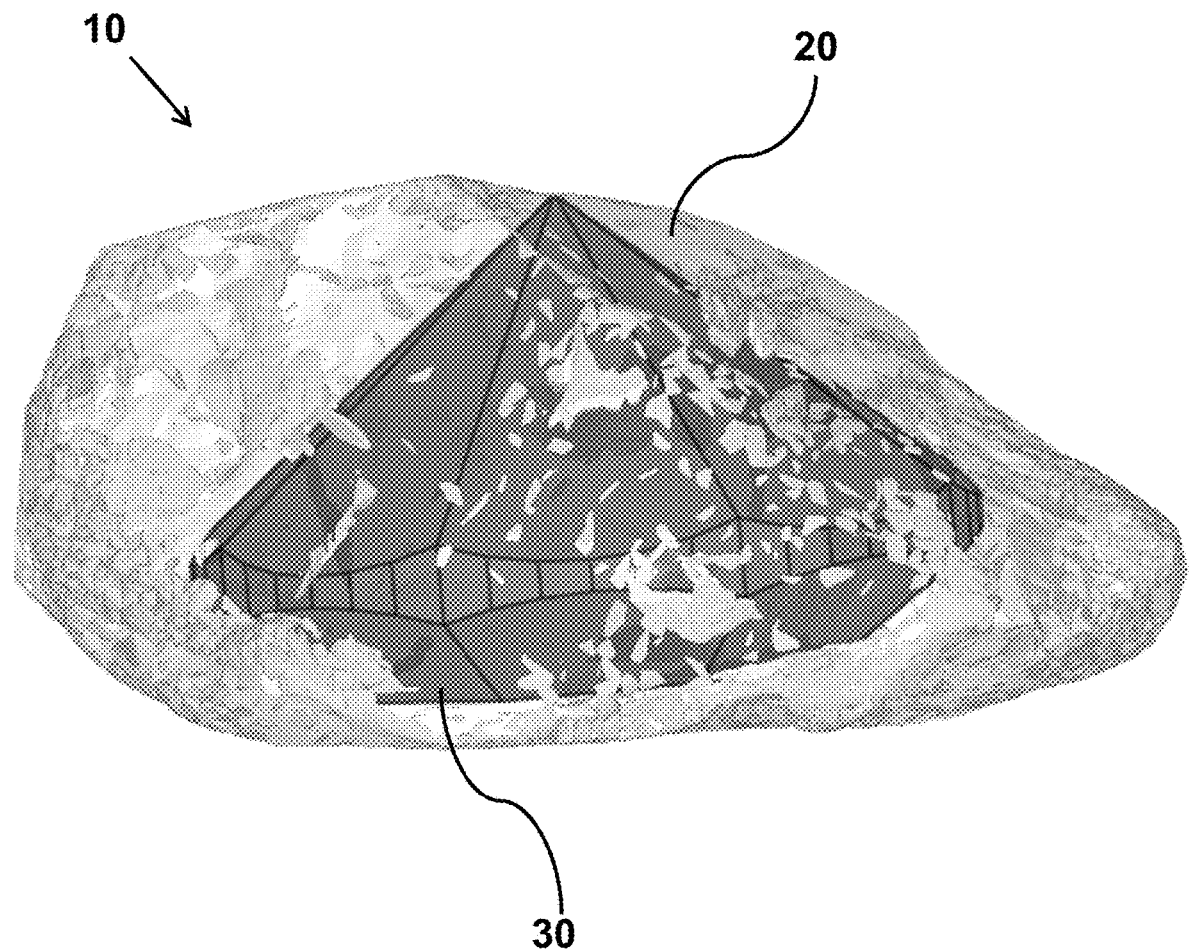
FIG. 1 illustrates a 3D model of a rough gemstone and a 3D model of a target stone to be cut from the rough stone.

Described herein with reference to FIGS. 1 to 4 is a method of determining an optimal faceted gemstone (target gemstone) to be cut from a rough gemstone. The method comprises obtaining a first series of 2D images of the rough gemstone; providing a 3D model of a target gemstone to be obtained from the rough gemstone; generating a second series of 2D images of the target gemstone from the 3D model; and comparing the first and second series of 2D images to determine an optimal transformation to be applied to the 3D model of the target gemstone. An apparatus for carrying out at least some steps of the method is also described.

It will be appreciated that, in the context of faceted gemstone production, "optimal" may be defined in various ways. For example, the "optimal" target stone may be the largest or heaviest target stone which is obtainable from the rough stone, or it may be the target stone which delivers the highest yield, where yield may be defined as the weight of the target stone divided by the weight of the rough stone. Other "optimal" target stones may be envisaged. Internal features of the rough stone, such as inclusions, may also have an impact upon the definition of "optimal".

In one example, the method comprises providing a 3D model of a rough gemstone which is to be cut to produce a target faceted gemstone. In this specific example, the "optimal" target stone is the largest stone which may be obtained from the rough gemstone. The 3D model may be a surface model, obtained by illuminating the rough gemstone with collimated light from one side and capturing 2D silhouette images of the gemstone from the opposite side to the illumination. This should be repeated at many different viewpoints. These 2D images are then combined into a single 3D model. In one non-limiting example, 2D images of the rough stone may be captured from twenty-one different viewpoints.

The rough gemstone may optionally be additionally illuminated with diffuse light. The information from the 2D images obtained under diffuse lighting (i.e. the diffuse images) may be captured from the same viewpoints and potentially at the same time as the silhouette images obtained under collimated lighting. The diffuse images can provide information regarding the texture and/or the interior of the rough stone, which can be incorporated into the 3D model formed from the silhouette images. This information may, for example, comprise the location of inclusions and other internal features of the stone which could affect the planned location of the target facet cuts. The information obtained from the 2D diffuse images may be used to optimise the 3D surface model of the stone.

In one example, the rough gemstone to be modelled is mounted on a rotatable mount and imaged by one or more stationary image capture devices (e.g. cameras) at a plurality of discrete rotational increments as the mount rotates. The rotatable mount may comprise a turntable, a vacuum nozzle, or the like, which ideally does not obscure any part of the rough gemstone to be modelled. Alternatively or additionally, the rough gemstone may be allowed to free fall past a plurality of image capture devices, arranged around the gemstone's free fall path. Each discrete view of the stone from which an image is captured, regardless of whether the stone is imaged by one or more cameras as it is rotated, or imaged by multiple cameras arranged around its freefall path, or otherwise, will be referred to as a "camera view".

Figure 2:
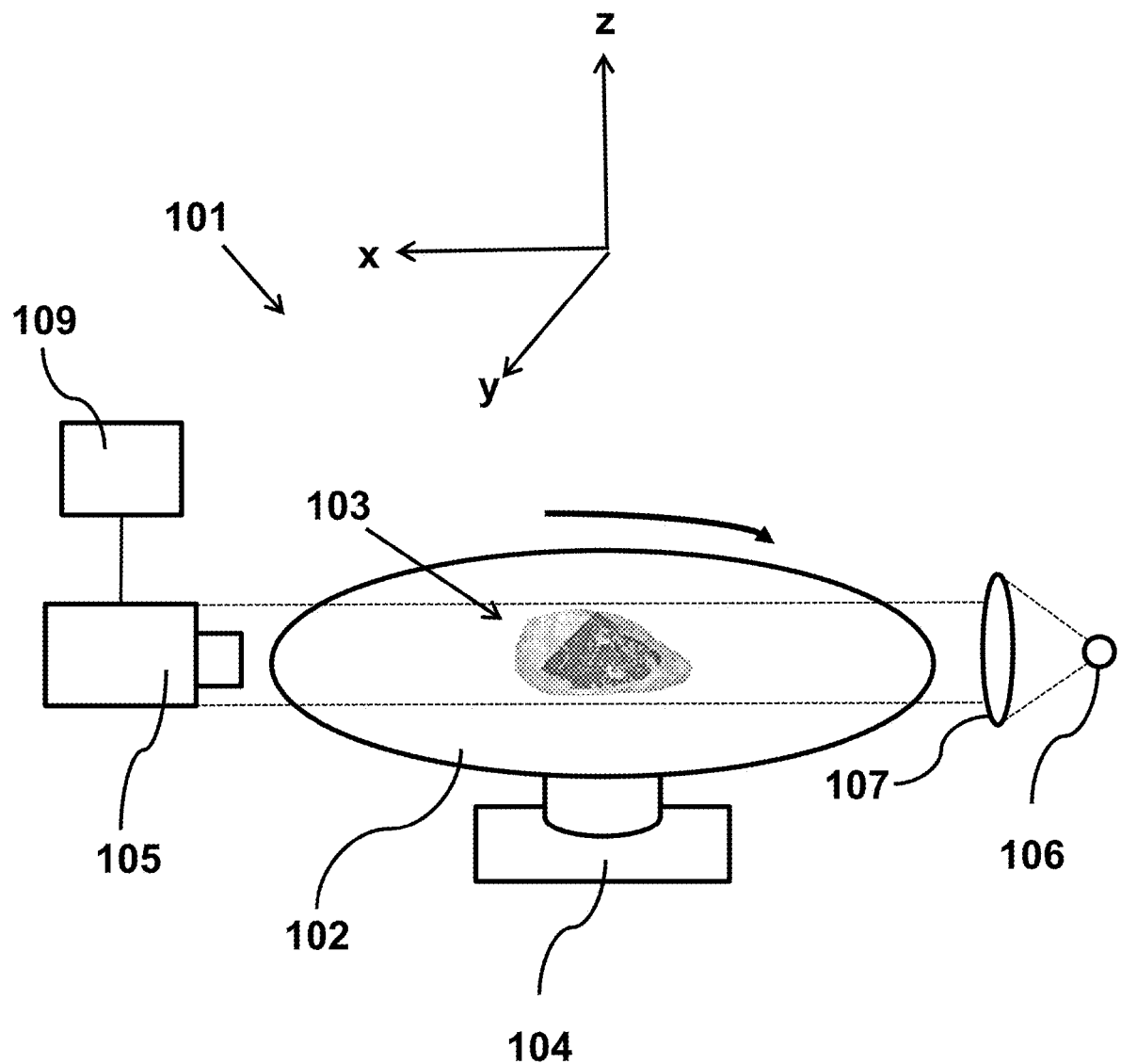
FIG. 2 illustrates an apparatus for obtaining images of a rough gemstone.

FIG. 2 illustrates a side view of an exemplary apparatus for capturing 2D images of a rough gemstone to be modelled. The apparatus 101 comprises a rotatable turntable 102 onto which a rough gemstone 103, such as a diamond, can be placed. A stepper motor 104 is used to rotate the turntable 102, and the gemstone 103 supported thereon, accurately through any specified angle.

Images of the gemstone 103 are captured at each predetermined angular interval or discrete rotational increment, i.e. at each required camera view, using a camera 105, such as for example a single ½" (8 mm diagonal) CCD, IEEE1394-interfaced digital camera with a resolution of 1280×960 pixels. In this illustrated example, the camera 105 is arranged such that it is directed at the side of the gemstone 103, i.e. so that the camera's image plane and the turntable are parallel to one another (co-planar). However, the camera or cameras may be provided in an alternative, non-co-planar arrangement around the rough stone. For example, multiple cameras may be provided in a spherical (e.g. geodesic) arrangement around the stone.

The camera 105 optics used may be telecentric, i.e. they collect only light incident parallel to their optical axis within a range of angles determined by their numerical aperture. The images obtained from the cameras 105 are exported to a processor 109 and stored on a storage device (not shown in FIG. 2).

In the exemplary apparatus of FIG. 2, the gemstone 103 is illuminated by collimated light provided by an LED 106 and associated optics 107. Collimated lighting allows the gemstone 103 to be seen completely in silhouette. It will be appreciated that the apparatus of FIG. 2 could be modified to incorporate a source of diffuse lighting, in cases where it may be desirable to capture a set of diffuse images of the gemstone at the same rotational positions i.e. the same camera views at which the silhouette images are obtained.

The exemplary apparatus 101 of FIG. 2 will now be described in use. The turntable 102, on which the gemstone 103 is supported, is rotated in discrete increments by the stepper motor 104. After each incremental rotation, i.e. for each camera view, at least one 2D silhouette image of the surface of the gemstone 103 under collimated lighting is captured by the camera 105. The set of captured 2D silhouette images of the rough stone, comprising captured images from each camera view, is transferred to the processor 109. It will be appreciated that the processor 109 may form part of the exemplary apparatus 101, or may be located separately and/or remotely from the apparatus 101.

At the processor 109, the silhouette images may be combined to construct a virtual 3D model (i.e. a surface model) of the rough gemstone. Methods of producing a 3D surface model from a set of 2D silhouette images are known in the art. The 3D model of the rough gemstone to be cut, if produced from the set of 2D silhouette images, is stored on the storage device. Again, the storage device may form part of the exemplary apparatus 101, or may be located separately and/or remotely.

A virtual 3D model of a target, faceted gemstone that is desired to be cut from the rough gemstone is then provided. In one example, this 3D model of the target gemstone is selected, or otherwise obtained, from an existing database of known polished cuts (e.g. round brilliant, emerald, princess etc.). This database may be stored on the above storage device. Alternatively, the selected model may be obtained from a database stored remotely. The selection of the target gemstone may be automatic, based upon an "optimal" target stone, or may be made manually, based upon other predetermined factors.

The virtual 3D model of the target gemstone comprises a polygon mesh. Each polygon represents one facet, or part of a facet, of the target stone. For example, the table of a round brilliant cut gemstone may be represented as an octagon. However, there is no requirement that each facet has to be represented as a single polygon. For example, each facet can be represented in the 3D model of the target gemstone by multiple connected triangles.

The processor is used to generate a set of virtual 2D silhouette images of the selected target gemstone. These virtual 2D images are obtained using virtual cameras "positioned" around the virtual 3D model of the target gemstone, such that the virtual camera views of the target stone from the virtual cameras are identical to the real camera views of the rough stone from the physical camera or cameras.

Figure 3A:
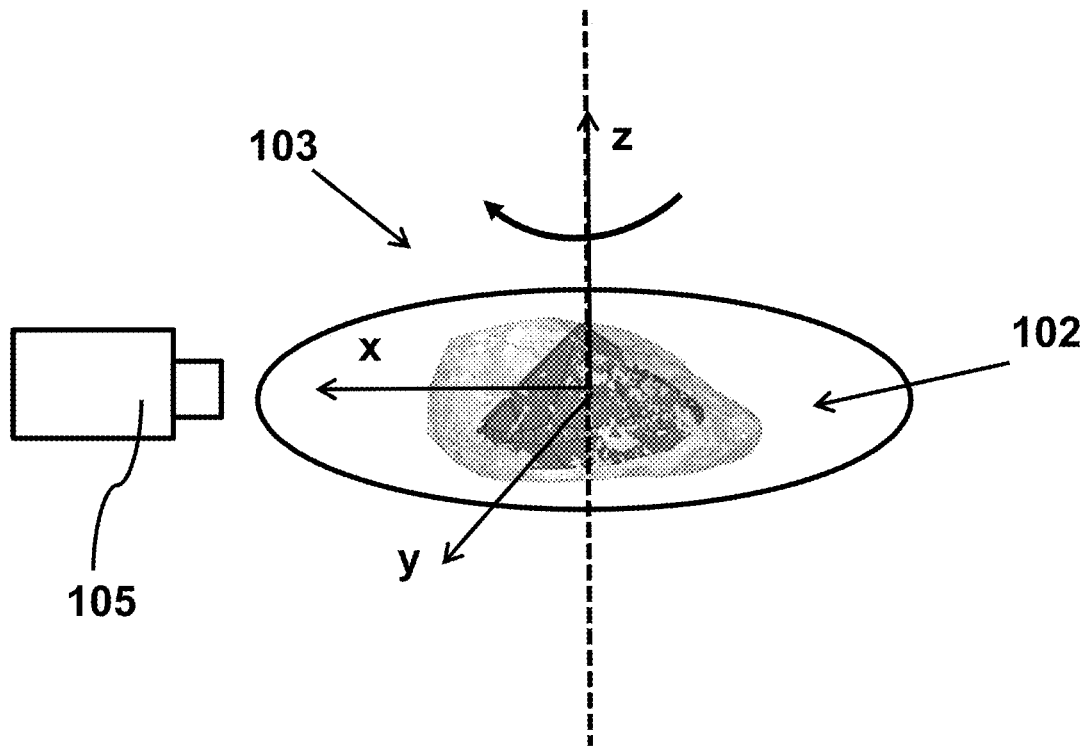
FIGS. 3a, 3b and 3c illustrate the positioning of real and virtual cameras around a rough gemstone and a 3D model of a target gemstone.
Figure 3B:
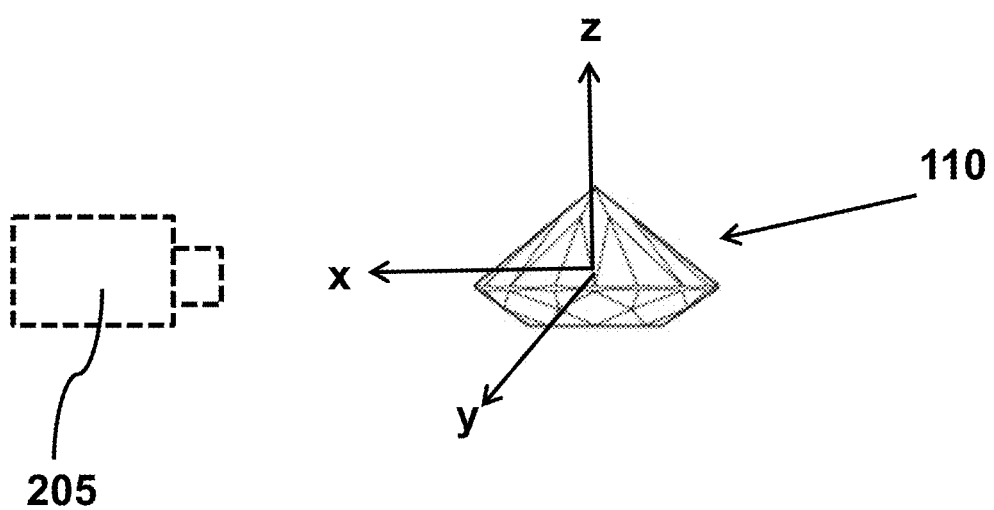

In one example, illustrated in FIGS. 3a and 3b, a single physical camera 105 is positioned to capture multiple camera views (i.e. 2D silhouette images) of the rough stone 103 as it is rotated on a turntable 102. A virtual camera 205 is "positioned" in an identical position to the physical camera 105 to provide multiple virtual camera views (i.e. 2D silhouette images) of the 3D model of the target gemstone 110 as it is virtually "rotated". The camera views captured by the physical camera 105 of the rough stone 103 and the camera views captured by the virtual camera 205 of the 3D model of the target gemstone 110 will therefore be captured from identical positions.

Figure 3C:
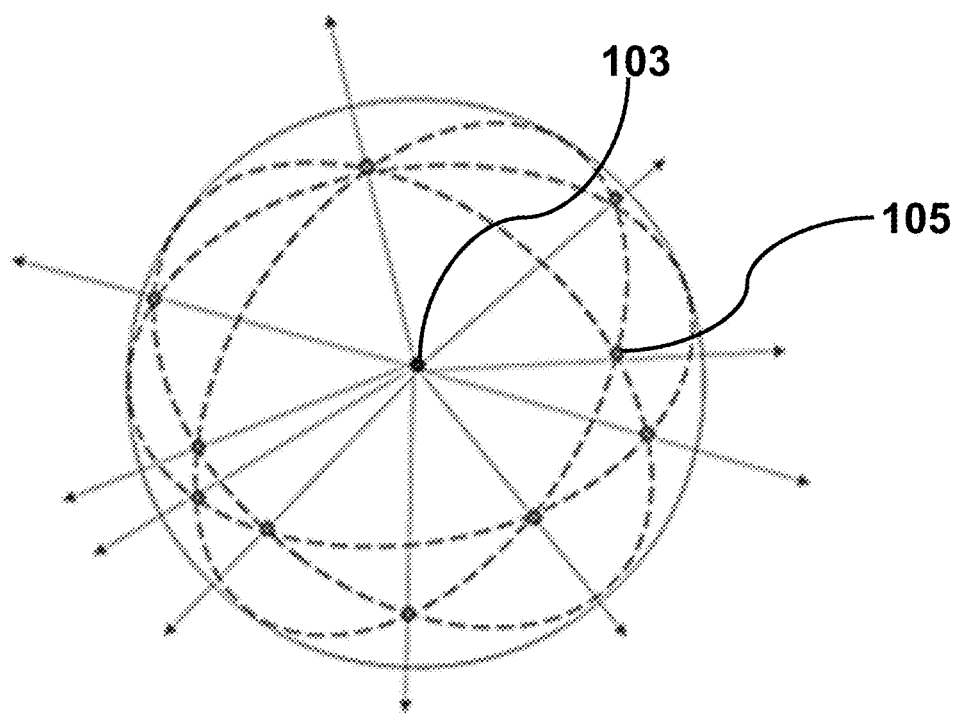

In an alternative example illustrated in FIG. 3c, a plurality of physical cameras 105 are positioned in a geodesic arrangement around the rough stone 103. The "position" of the virtual cameras around the 3D model of the target stone in this example will be identical.

It will be appreciated that the virtual 2D silhouette images are generated by the processor to provide virtual views of the selected target gemstone. At this stage, of course, the target gemstone has yet to be cut from the rough stone.

The exemplary method described above therefore comprises obtaining at least the following sets of images:

A: a set of real 2D silhouette images captured from different camera views under collimated lighting of the rough stone, from which a 3D model of the rough stone may be generated; and B: a set of virtual 2D silhouette images, captured from the same camera views, of the selected target gemstone generated by virtual cameras "arranged" around a selected 3D model of a target gemstone.

A correlation between sets A and B may be determined as follows. Referring back to FIGS. 3a and 3b, the world XYZ coordinates may be chosen such that: the Z axis may coincide with the rotation axis of the rotatable turntable 102, and the XY plane may be parallel to the rotatable turntable 102. The X axis of the world coordinates may be chosen to be parallel to the camera's 105 image plane and the Y axis of the world coordinates may be perpendicular to the camera's 105 image plane. It will be appreciated, however, that the assignment of these coordinates is purely arbitrary in order to facilitate discussion of the transformation to be applied.

Assuming that the rotatable turntable 102 has a flat horizontal support surface which obscures no part of the rough gemstone 103, it may be assumed that the 2D silhouette images of the rough gemstone (set A) each have a vertical centre at the silhouette image centre. It may be further assumed that the origin of the world XYZ coordinates is aligned with all of the rough stone 2D silhouette image centres. That is, if the world origin is projected onto each camera image plane, it falls at the image centre. Again, this assumption is purely for convenience of discussion.

With regard to the selected virtual 3D model of the target gemstone, it may be further assumed that the geometric centre of this 3D model is coincident with the world XYZ origin. In other words, the geometric centre of the 3D target model coincides with all of the real 2D silhouette image centres. This can be achieved as follows: (a) calculate the geometric centre (i.e. the centroid) of the virtual 3D model of the target gemstone by averaging all vertices (b) subtract all vertices with the estimated geometric centre.

Once a 3D model of the rough stone has been obtained, and a desired virtual 3D model of a target stone to be cut from the rough stone has been selected, it is necessary to determine: a) whether the selected target gemstone can in fact be cut from the rough gemstone; and b) if so, the set of transformations (scaling, translational and rotational) that must be applied to the virtual 3D target model in order to produce the optimal target gemstone from the rough material.

Determination of scale factors to be applied to the virtual 3D model of the target gemstone, which may be carried out at the processor, may be used to identify the optimal target gemstone that can be produced from the rough stone and to minimise waste material. A scale factor may decrease as well as increase the size of the 3D model.

Determination of a first initial scale factor S1 comprises projecting each virtual 2D silhouette image of the selected target gemstone into the corresponding real 2D silhouette image of the rough stone, where "corresponding image" refers to the real 2D image obtained from the identical camera view.

In one example, the determination of the first initial scale factor S1 is carried out as follows:
Step 1 Project each virtual 2D silhouette image of the selected target gemstone into the corresponding real 2D silhouette image of the rough stone;
Step 2 Find the bounding box of the projected virtual 2D silhouette image and the bounding box of the corresponding 2D real silhouette, wherein a bounding box is the smallest quadrilateral shape within which all points of the 2D silhouette images will fit;
Step 3 Calculate the ratio between the widths of these two bounding boxes;
Step 4 Calculate the ratio between the heights of the two bounding boxes;
Step 5 Choose the maximum of the two ratios as calculated in Step 3 and Step 4 above;
Step 6 Apply the above steps to all of the camera views i.e. for all of the virtual 2D silhouette images of the target stone, determining one maximum ratio for each camera view;
Step 7 Find the largest maximum ratio from all of the determined maximum ratios for all of the virtual camera views;
Step 8 Determine the first scale factor S1 by adding a positive value, or multiplying a value larger than 1, to the largest maximum ratio as determined in Step 7.

Clearly, if scale S1, as determined above, is applied to the selected 3D model of the target gemstone, the virtual 2D silhouette images derived from this first scaled 3D model of the target gemstone will be too large to fit inside all of the corresponding real 2D silhouette images of the rough gemstone, i.e. it will be too large to fit within the rough gemstone.

Figure 4A:
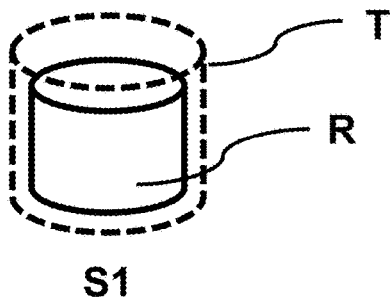
FIGS. 4a, 4b and 4c illustrate methods of determining a scaling factor to be applied to a 3D model of a target gemstone.

In other words, as illustrated in FIG. 4a, regardless of any rotational or translational transformations which may be applied to the virtual 3D target model by the processor, a target gemstone T scaled by factor S1 cannot be cut from the real rough gemstone R. (In this illustrated example, both the target and rough stones are represented as cylinders for simplicity). Initial scale factor S1 therefore represents a scale factor that is too large.

Determination of a second initial scale factor S2 is now carried out. S2 is a relatively small scale factor, at which there is at least one combination of translational and rotational transformations that will allows all virtual 2D silhouette images of the 3D target model to fit inside all real 2D silhouette images of the rough gemstone.

In one example, determination of the second initial scale factor S2 is carried out as follows:
Step 9 Initially set S2 as S1, as determined above at Step 8;
Step 10 Multiply S2 by 0.5;
Step 11 Scale the virtual 3D target model by S2*0.5, without applying any rotational or translational transformations;
Step 12 Generate a scaled set of virtual 2D silhouette images of the selected target gemstone from the scaled 3D target model from Step 11, using the virtual camera views as previously described;
Step 13 Project each scaled virtual 2D silhouette image of the selected target gemstone into the corresponding real 2D silhouette image of the rough stone;
Step 14 If at least one of the scaled virtual 2D silhouette images fails to fit inside its corresponding real 2D silhouette image, return to the multiplication step 10 above and repeat the process (i.e. multiply S2 by increasing increments of 0.5), until a value of S2 is found at which all of the virtual 2D silhouette images to which the scale factor S2 is applied fit inside the real 2D silhouette images.

Figure 4B:
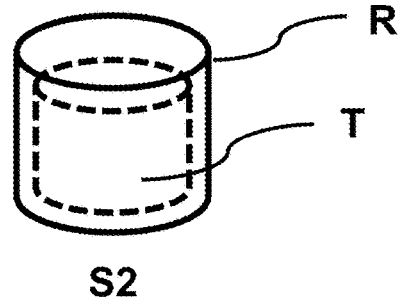

Initial scale factor S2 therefore represents a scale factor which is sufficiently small to enable the scaled target gemstone T to be cut from the rough stone R, as illustrated in FIG. 4b. Again, the target and rough stones are illustrated as cylinders for simplicity.

The determination of the initial scale factors S1 and S2 therefore comprises determining a scale factor at which (i) no virtual 2D images of the selected target gemstone fit within the corresponding real 2D silhouette images of the rough stone (S1) and (ii) all virtual 2D images of the selected target gemstone fit within the corresponding real 2D silhouette images of the rough stone (S2). This can be considered as a binary selection i.e. all images fit or not all images do not fit.

Application of initial scale factor S2 to the 3D model of the target gemstone, as determined above, would ensure that all of the virtual 2D silhouette images fit inside the corresponding real 2D silhouette images. It therefore follows that the virtual 3D model of the target gemstone, scaled to the same factor, would fit inside the 3D model of the rough stone, i.e. the target gemstone at this scale factor can be cut from the rough stone. However, the target gemstone at this scale factor may not be the optimal target gemstone, i.e. the target gemstone at this scale factor may not be the largest stone that can be cut from the rough stone.

Once initial scale factors S1 and S2 have been determined, it is therefore necessary to refine the scale factor to be applied to the 3D model of the target gemstone, in order to optimise the cut and minimise waste material.

Figure 4C:
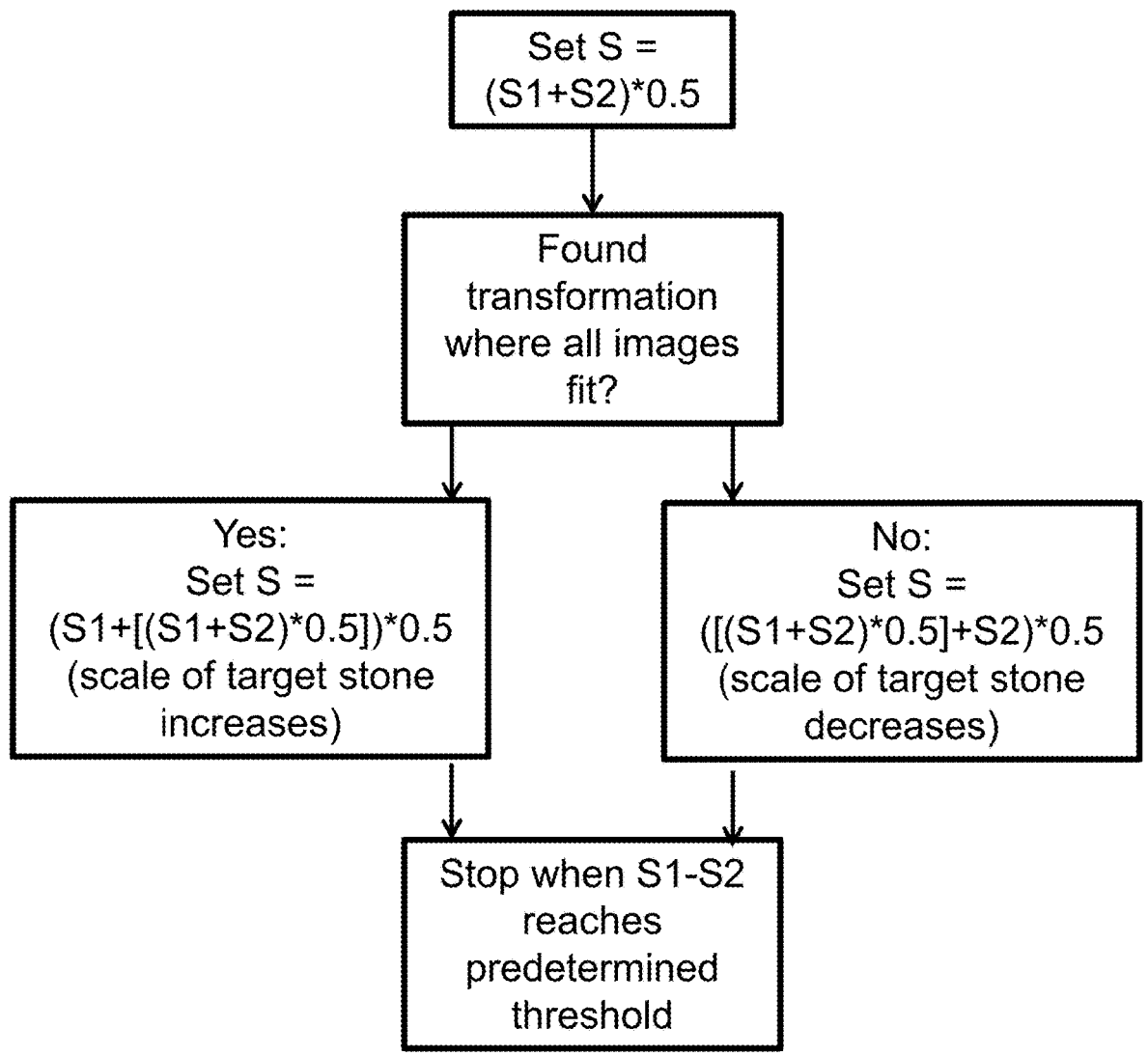

As illustrated in FIG. 4c, in one example, final scale factor S is determined as follows:
Step 15 Initially set S as (S1+S2)*0.5 (i.e. a scale factor midway between S1 and S2, or the average of S1 and S2);
Step 16 Apply scale factor S from Step 15 to the virtual 3D model of the target gemstone;
Step 17 Enumerate all combinations of translational and rotational transformations of the 3D model of the target gemstone, wherein the translation step may be set as small as one pixel, and the rotations may be digitised with a constant small angle;
Step 18 For each combination enumerated in Step 17, generate a transformed set of virtual 2D silhouette images of the selected target gemstone from the 3D target model scaled by S, using the virtual camera views as previously described;

Step 19 Compare all of transformed virtual 2D silhouette images from Step 18 with their corresponding real 2D silhouette images;

Step 20 If there is any one combination of translational and rotational transformations found wherein all the virtual 2D silhouette images fall inside all of the real 2D silhouette images, record the translation and rotation for this specific combination. Return to Step 15, set S2 as S from Step 16 and repeat the process.

Step 21 Alternatively, if no combination can be found wherein all virtual 2D silhouette images fall inside all the real 2D silhouette images, then return to Step 15, set S1 as S from Step 16 and repeat the process.

Step 22 When (S1-S2) is smaller than a predefined threshold, terminate the iteration. The numerical value of the predefined threshold depends on the initial size of the target gemstone. Initially the target gemstone is assumed to have a standard size, such that it can be placed inside a sphere which has a radius of 1, with the geometric centre of the target gemstone at the sphere centre. Then the typical scale threshold is 0.001. Final scale factor S can be taken as the last value of S2. Together with the last recorded translation and rotation, scale factor S defines the best fit target model i.e. the optimal target stone that can be cut from the rough stone.

In Step 20, it will be appreciated that, having found a transformation at which all virtual images fit inside all real images, it is desirable to increase the final scaling factor S to see whether a larger target stone is possible. Thus, S2 (the scaling factor at which the target stone definitely fits within the rough stone) is replaced by scale factor midway between S1 and S2. The target stone scale is thereby increased.

In Step 21, it will be appreciated that, having found no transformations at which all virtual images fit inside all real images, it is desirable to decrease the final scaling factor S to find a smaller target stone that may fit inside the rough stone. Thus, S1 (the scaling factor at which the target stone is too large to fit within the rough stone) is replaced by scale factor midway between S1 and S2. The target stone scale is thereby decreased.

In Step 22, the iteration is stopped when the difference between the scaling factor at which the target stone is too large and the scaling factor at which the target stone fits reaches a predetermined value. At this point, the last value of S2 (the scaling factor at which the target stone fits) is taken as the final scale S, together with the translation and rotation that accompanied that value. The predetermined value for the difference between S1 and S2 allows for a margin of error.

The method described herein, and the exemplary apparatus for carrying out at least a part of this method, enables an optimal target stone to be planned and cut from a rough stone. Moreover, since this method encompasses the comparison of 2D images with 2D images, it is less resource intensive in terms of computational processing that a conventional method which compares images in 3D space.

Once the optimal target stone has been determined, a final 3D model comprising the rough gemstone and the determined optimal target gemstone may be generated. This final 3D model may be stored for future use.

The process described above has been set out in terms of fitting a set of 2D images of a virtual target gemstone into a set of 2D silhouette images of a real rough gemstone. It will be appreciated that a virtual model of a 3D rough stone may also be used as a starting point. Such a model may have itself been prepared from 2D silhouette images, but these may no longer be available. In this instance a set of "virtual" 2D silhouette images of the model of the rough stone may be calculated in the same way as the virtual 2D images of the target stone. The 2D images of the target stone may then be correlated with the 2D images of the rough stone model in the same manner described above. This will still be less resource intensive than comparing images in 3D space.

When determining whether a virtual 2D silhouette image of a target gemstone fits entirely within a real 2D silhouette image of a rough stone, it will be appreciated that under certain circumstances a portion of the outer surface of the rough gemstone may ultimately form a portion of a facet of the cut, target gemstone. Therefore, the 3D model of the target gemstone must fit entirely inside the 3D model of the rough gemstone in the sense that no part of the surface of the target gemstone extends beyond the outer surface of the rough gemstone.

The processor and/or the storage unit as described herein may be comprised in one or more standalone or networked computer systems.

As described herein, "rough" refers to a gemstone, such as a diamond, which is substantially uncut.

As described herein, "real" refers to an image of a physical object captured by a physical image capture device. As described herein "virtual" refers to an image which is generated by software and is not a directly captured image of a physical object.

The invention claimed is:

1. A method of determining an optimal target gemstone to be obtained from a rough gemstone, the method comprising:
   obtaining a first series of two-dimensional (2D) silhouette images of the rough gemstone;
   providing a three-dimensional (3D) model of a target gemstone to be obtained from the rough gemstone;
   generating a second series of virtual 2D silhouette images of the target gemstone from the 3D model of the target gemstone; and
   comparing the first series of 2D silhouette images and the second series of virtual 2D silhouette images to determine an optimal transformation to be applied to the 3D model of the target gemstone.

2. The method of claim 1, wherein the first series of 2D silhouette images and the second series of virtual 2D silhouette images are obtained from the same positions.

3. The method of claim 1, further comprising correlating the first series of 2D silhouette images and the second series of virtual 2D silhouette images before comparing the first series of 2D silhouette images and the second series of virtual 2D silhouette images.

4. The method of claim 3, wherein correlating the first series of 2D silhouette images and the second series of virtual 2D silhouette images comprises setting a geometric centre of the 3D model of the target gemstone to be coincident with an image centre of each of the first series of 2D silhouette images.

5. The method of claim 1, wherein obtaining the first series of 2D silhouette images of the rough gemstone comprises illuminating the rough gemstone with collimated light and capturing a 2D silhouette image of the rough gemstone at each of a plurality of discrete rotational increments.

6. The method of claim 5, further comprising rotating the rough gemstone as the first series of 2D silhouette images is obtained.

7. The method of claim 5, further comprising obtaining a third series of 2D images of the rough gemstone under diffuse lighting, each of the third series of 2D images being captured at each of the plurality of discrete rotational increments.

8. The method of claim 1, wherein obtaining the first series of 2D silhouette images of the rough gemstone comprises generating 2D silhouette images from a 3D model of the rough gemstone.

9. The method of claim 1, wherein providing the 3D model of the target gemstone comprises selecting a 3D model from a plurality of 3D models of cut and faceted gemstones.

10. The method of claim 1, wherein generating the second series of virtual 2D silhouette images of the target gemstone from the 3D model of the target gemstone comprises virtually positioning a plurality of virtual cameras around the 3D model of the target gemstone, each virtual camera configured to capture one or more 2D silhouette images of the target gemstone from a respective position of the virtual camera.

11. The method of claim 10, further comprising positioning the plurality of virtual cameras in a geodesic arrangement around the 3D model of the target gemstone.

12. The method of claim 10, further comprising virtually illuminating the 3D model of the target gemstone with collimated light.

13. The method of claim 1, wherein comparing the first series of 2D silhouette images and the second series of virtual 2D silhouette images to determine an optimal transformation to be applied to the 3D model of the target gemstone comprises:
projecting each 2D silhouette image of the second series of virtual 2D silhouette images into a corresponding 2D silhouette image of the first series of 2D silhouette images, wherein the corresponding 2D silhouette images of the first series of 2D silhouette images and the second series of virtual 2D silhouette images are captured from the same positions;
determining a first scaling factor, which when applied to each of the second series of virtual 2D silhouette images produces a first scaled second series of virtual 2D silhouette images, each of the first scaled second series of virtual 2D silhouette images is too large to fit inside the corresponding 2D silhouette image of the first series of 2D silhouette images; and
determining a second scaling factor which, when applied to the each of the second series of virtual 2D silhouette images, produces a second scaled series of 2D silhouette images, each of the second scaled second series of virtual 2D silhouette images fits inside the corresponding 2D silhouette image of the first series of 2D silhouette images.

14. The method of claim 13, wherein comparing the first series of 2D silhouette images and the second series of virtual 2D silhouette images to determine an optimal transformation to be applied to the 3D model of the target gemstone further comprises:
determining an average of the first scaling factor and the second scaling factor to produce a third scaling factor;
applying the third scaling factor to the 3D model of the target gemstone to generate a scaled 3D model;
determining combinations of translational and rotational transformations of the 3D model of the target gemstone;
for each combination of translational and rotational transformations, generating a series of transformed and scaled 2D silhouette images of the target gemstone from the scaled 3D model;
for each combination of translational and rotational transformations, projecting each 2D silhouette image of the series of transformed and scaled 2D silhouette images of the target gemstone into the corresponding 2D silhouette image of the first series of 2D silhouette images; and
iteratively increasing or decreasing the third scaling factor to identify a combination of translational and rotational transformations, wherein each of the 2D silhouette images of the series of transformed and scaled 2D silhouette images of the target gemstone fits within the corresponding 2D silhouette image of the first series of 2D silhouette images, and wherein a difference between the first scaling factor and the second scaling factor is smaller than a predetermined threshold.

15. The method of claim 14, further comprising applying the identified combination of translational, rotational and scaling transformations to the 3D model of the target gemstone.

16. The method of claim 1, wherein the optimal target gemstone corresponds to a largest target gemstone that is obtainable from the rough gemstone.

17. The method of claim 1, wherein the rough gemstone is a diamond.

18. The method of claim 1, further comprising generating a 3D model of the rough gemstone that comprises the optimal target gemstone to be obtained from the rough gemstone.

19. A method of determining an optimal target gemstone to be obtained from a rough gemstone, the method comprising:
obtaining a first series of two-dimensional (2D) silhouette images of the rough gemstone;
providing a three-dimensional (3D) model of a target gemstone to be obtained from the rough gemstone;
generating a second series of virtual 2D silhouette images of the target gemstone from the 3D model of the target gemstone;
comparing the first series of 2D silhouette images and the second series of virtual 2D silhouette images to determine an optimal transformation to be applied to the 3D model of the target gemstone; and
fitting each image of the second series of virtual 2D silhouette images into a corresponding image of the first series of 2D silhouette images to determine if the target gemstone fits into the rough gemstone.

20. The method of claim 19, wherein corresponding images of the first series of 2D images and the second series of virtual 2D images comprise images captured from the same positions.

21. An apparatus for determining an optimal target gemstone to be obtained from a rough gemstone, the apparatus comprising:
one or more image capture devices configured to obtain a first series of two-dimensional (2D) silhouette images of the rough gemstone; and
a processor configured to:
generate a second series of virtual 2D silhouette images from a three-dimensional (3D) model of a target gemstone to be obtained from the rough gemstone; and
compare the first series of 2D silhouette images and the second series of virtual 2D silhouette images to determine an optimal transformation to be applied to the 3D model of the target gemstone.

* * * * *